United States Patent
Klass et al.

(10) Patent No.: US 7,670,464 B2
(45) Date of Patent: Mar. 2, 2010

(54) METHOD FOR THE DISTILLATIVE SEPARATION OF A MIXTURE CONTAINING VINYL ETHER AND ALCHOL

(75) Inventors: Katrin Klass, Mannheim (DE); Heike Becker, Mannheim (DE); Regina Vogelsang, Ludwigshafen (DE); Alexander Hauk, Ludwigshafen (DE); Markus Siegert, Heidelberg (DE); Jochem Henkelmann, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 948 days.

(21) Appl. No.: 10/560,135

(22) PCT Filed: Jun. 8, 2004

(86) PCT No.: PCT/EP2004/006160

§ 371 (c)(1),
(2), (4) Date: Dec. 9, 2005

(87) PCT Pub. No.: WO2004/110970

PCT Pub. Date: Dec. 23, 2004

(65) Prior Publication Data

US 2006/0151310 A1 Jul. 13, 2006

(30) Foreign Application Priority Data

Jun. 12, 2003 (DE) .................................. 103 26 403

(51) Int. Cl.
*B01D 3/36* (2006.01)
*C07C 29/82* (2006.01)
*C07C 41/42* (2006.01)
*C07C 43/16* (2006.01)
*C07C 41/08* (2006.01)

(52) U.S. Cl. .............................. 203/73; 203/75; 203/77; 203/78; 203/80; 203/99; 203/DIG. 19; 568/579; 568/689; 568/913

(58) Field of Classification Search .................. 202/158; 203/73, 75, 77, 78, 80, 99, DIG. 19; 568/579, 568/689, 913
See application file for complete search history.

(56) References Cited

U.S. PATENT DOCUMENTS

| 2,760,990 A | * | 8/1956 | Conlon et al. ................ 568/589 |
| 2,779,720 A | | 1/1957 | Tanona |
| 3,878,058 A | | 4/1975 | Tanaka |

FOREIGN PATENT DOCUMENTS

| DE | 1 000 804 | 1/1957 |
| EP | 0 415 334 | 3/1991 |
| JP | 10 109952 | 4/1998 |
| SU | 1 616 888 | 12/1990 |
| WO | 00/15590 | 3/2000 |

OTHER PUBLICATIONS

Coulson et al "Chemical Engineering" vol. Two, Third Ed., 1978, p. 478.*
Ullmann's Encyclopedia of Industrial Chemistry, 6$^{th}$ Edition, Electronic Release, Chapter, "Vinyl Ethers—Production", 2000.
Reppe, Walter et al., Justus Liebigs Annalen der Chemie 601, pp. 81 to 111, 1956.

* cited by examiner

*Primary Examiner*—Virginia Manoharan
(74) *Attorney, Agent, or Firm*—Oblon, Spivak, McClelland, Maier & Neustadt, L.L.P.

(57) ABSTRACT

Process for distillatively separating a mixture containing a vinyl ether of the general formula (I)

$$R^1-O-CH=CH_2 \qquad (I)$$

and alcohol of the general formula (II)

$$R^2-OH \qquad (II)$$

in which $R^1$ and $R^2$ are each independently a saturated or unsaturated, aliphatic or cycloaliphatic radical having from 2 to 10 carbon atoms, and in which the alcohol (II) has a boiling point which is at least 1° C. higher, measured at or extrapolated to 0.1 MPa abs, than the vinyl ether (I), by a) passing the mixture into a first distillation column and withdrawing, as a top product, an azeotrope containing vinyl ether (I) and alcohol (II) and, as a bottom product, a stream enriched with the alcohol (II);

b) passing the azeotrope containing vinyl ether (I) and alcohol (II) from the first distillation column into a second distillation column which is operated at a pressure which is from 0.01 to 3 MPa higher compared to the first distillation column, and withdrawing, as a bottom product or gaseous sidestream in the stripping section, the vinyl ether (I) and, as a top product, an azeotrope containing vinyl ether (I) and alcohol (II); and c) recycling the azeotrope containing vinyl ether (I) and alcohol (II) from the second distillation column into the first distillation column.

10 Claims, 2 Drawing Sheets

METHOD FOR THE DISTILLATIVE SEPARATION OF A MIXTURE CONTAINING VINYL ETHER AND ALCHOL

BACKGROUND OF THE INVENTION

The present invention relates to a process for distillatively separating a mixture containing a vinyl ether of the general formula (I)

$$R^1\text{—O—CH=CH}_2 \qquad \text{(I)}$$

and alcohol of the general formula (II)

$$R^2\text{—OH} \qquad \text{(II)}$$

in which $R^1$ and $R^2$ are each independently a saturated or unsaturated, aliphatic or cycloaliphatic radical having from 2 to 10 carbon atoms, and in which the alcohol (II) has a boiling point which is at least 1° C. higher, measured at or extrapolated to 0.1 MPa abs, than the vinyl ether (I).

Vinyl ethers constitute an important compound class having a wide field of use. For instance, they find use, inter alia, as monomer building blocks in polymers and copolymers, in coatings, adhesives, printing inks and in radiation-curative coating materials. Further fields of use are the preparation of intermediates, fragrances and flavors, and also pharmaceutical products.

Vinyl ethers are generally prepared industrially by reacting the appropriate alcohols with ethyne in the presence of basic catalysts (see Ullmann's Encyclopedia of Industrial Chemistry, 6$^{th}$ edition, 2000 Electronic Release, Chapter "VINYL ETHERS—Production" and W. Reppe et al., Justus Liebigs Ann. Chem., 601 (1956), pages 135 to 138). In addition to the catalyst and possible by-products, the reaction mixture formed comprises mainly the vinyl ether formed and the unconverted alcohol. The two latter components, apart from the $C_1$ derivatives, methyl vinyl ether/methanol, cannot be separated by simple distillation into fractions of the desired purity as a consequence of azeotrope formation. This problem has hitherto been solved by the use of extraction and extraction distillation processes, in which one or more extraneous substances are added as auxiliaries and then removed again after separation into a vinyl ether- and an alcohol-containing fraction.

For instance, EP-A 0 415 334 describes the one- or multistage extraction of a vinyl ether- and alcohol-containing mixture with an aqueous solution of a base, in which a vinyl ether phse and an aqueous alcoholic phase are obtained and the alcohol is then obtained by distillation from the aqueous alcoholic phase.

U.S. Pat. No. 2,779,720 describes a process for separating a mixture which comprises an aliphatic vinyl ether and an aliphatic alcohol, in which this mixture is distilled together with water and a glycol or glycol ether. The top product formed in this case is an azeotropic mixture of the vinyl ether and water, from which the vinyl ether can be obtained in a further distillation. The bottom product remaining is a mixture comprising the alcohol and glycol or glycol ether, from which the alcohol can be obtained by a downstream distillation.

DE-A 1 000 804 discloses a process for working up a mixture which comprises a monovinyl ether of a polyhydric alcohol and a polyhydric alcohol, in which this mixture is distilled together with water in an alkaline medium or subjected to a steam distillation. The top product obtained in this case is an azeotropic mixture of the vinyl ether with water, and the residue remaining in the bottom is the alcohol. The top fraction obtained in the distillation may optionally be extracted with a water-immiscible solvent to transfer the vinyl ether to the organic phase, from which it can be obtained by distillation.

SU 1 616 888 describes the separation of a butanol- and butyl vinyl ether-containing mixture by extractive distillation with water. The azeotropic mixture formed as a top product which contains the butyl vinyl ether and water is subsequently distilled to obtain the butyl vinyl ether. The butanol-containing bottom product of the first distillation is worked up in a further distillation to obtain butanol.

U.S. Pat. No. 3,878,058 describes a process for obtaining alkyl vinyl ethers from a mixture containing the alkyl vinyl ether and an aliphatic alcohol, in which this mixture is distilled together with a glycol monoether. In this process, the top product removed is the alkyl vinyl ether and the bottom product obtained is an alcohol- and glycol monoether-containing mixture. This is separated in a subsequent distillation into the alcohol and the glycol monoether, and the latter is recycled to the first distillation stage.

A disadvantage of all of the abovementioned processes is the use of one or more extraneous substances as auxiliaries. This adds new compounds to the system which subsequently have to be removed again. This is associated firstly with corresponding cost and inconvenience relating to the apparatus and process, and secondly with the risk of contamination of the vinyl ether and/or of the alcohol by residual amounts of these extraneous substances. In addition, as a consequence of their intrinsic volume, the extraneous substances reduce the capacity of the distillation apparatus or require the use of larger distillation apparatus.

BRIEF SUMMARY OF THE INVENTION

It is an object of the present invention to find a process for separating a mixture comprising a vinyl ether and alcohol, which does not have the abovementioned disadvantages and leads to purified vinyl ether and alcohol, in particular at low cost and inconvenience with regard to apparatus and process, with high plant capacity and without the risk of contamination of the vinyl ether and/or the alcohol by the addition of extraneous substances as auxiliaries.

We have found that this object is achieved by a process for distillatively separating a mixture of a vinyl ether of the general formula (I)

$$R^1\text{—O—CH=CH}_2 \qquad \text{(I)}$$

and alcohol of the general formula (II)

$$R^2\text{—OH} \qquad \text{(II)}$$

in which $R^1$ and $R^2$ are each independently a saturated or unsaturated, aliphatic or cycloaliphatic radical having from 2 to 10 carbon atoms, and in which the alcohol (II) has a boiling point which is at least 1° C. higher, measured at or extrapolated to 0.1 MPa abs, than the vinyl ether (I), which comprises a) passing the mixture into a first distillation column and withdrawing, as a top product, an azeotrope containing vinyl ether (I) and alcohol (II) and, as a bottom product, a stream enriched with the alcohol (II);

b) passing the azeotrope containing vinyl ether (I) and alcohol (II) from the first distillation column into a second distillation column which is operated at a pressure which is from 0.01 to 3 MPa higher compared to the first distillation column, and withdrawing, as a bottom product or gaseous sidestream in the stripping section, the vinyl ether (I) and, as a top product, an azeotrope containing vinyl ether (I) and alcohol (II); and c) recycling the azeotrope containing vinyl ether (I) and alcohol (II) from the second distillation column into the first distillation column.

DETAILED DESCRIPTION OF THE INVENTION

Figure 1:
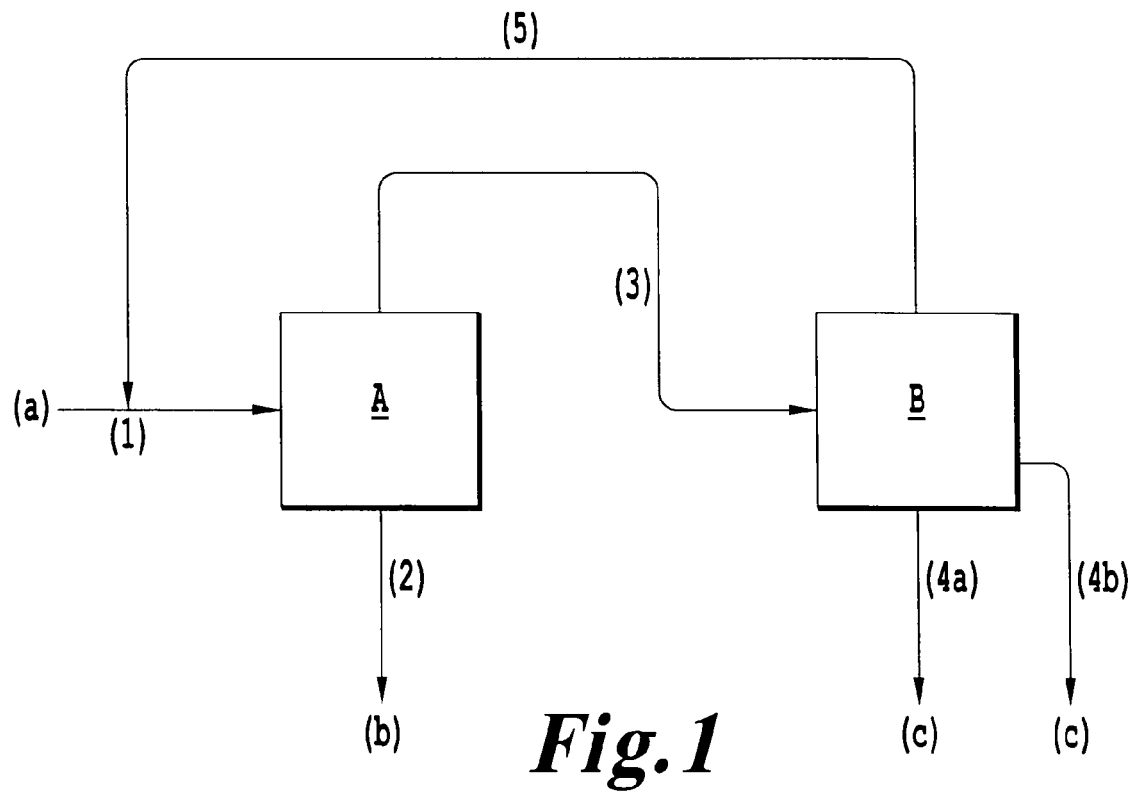
FIG. 1 shows a block diagram of the process of the invention.

The process according to the invention thus comprises two distillation columns. In the first distillation column, the mixture to be used which comprises vinyl ether (I) and alcohol (II) is separated into an azeotrope containing vinyl ether (I) and alcohol (II) as the top product and a stream enriched with the alcohol (II) as the bottom product.

In general, the first distillation column is operated at a temperature of from 75 to 225° C. and preferably from 100 to 175° C., measured in the bottom of the column, the temperature to be selected depending mainly upon the vinyl ether (I) and alcohol (II) to be separated and the selected pressure in the distillation column. In general, the first distillation column is operated at a pressure of from 0.01 to 1 MPa abs and preferably from 0.05 to 0.5° MPa abs, measured at the top of the column, the pressure to be selected depending mainly upon the vinyl ether (I) and alcohol (II) to be separated and the selected temperature in the distillation column. The temperature to be selected and the pressure to be selected in each case for a specific system may be determined by those skilled in the art by simple calculation or simple routine experiments. For each specific system, there exists a relationship between temperature and pressure, so that the parameter range to be employed is generally dictated by technical (for example design of the distillation column), economic (for example capital costs and/or energy costs) and chemical (for example only insignificant, if any, decomposition of the products), boundary conditions.

In general, the number of theoretical plates in the first distillation column is from 5 to 75, the number of theoretical plates to be used for a specific system depending mainly upon the vinyl ether (I) and alcohol (II) to be separated, and also upon the separating performance expected. The number of theoretical plates to be selected in each case for a specific system may be determined by those skilled in the art by simple calculation or simple routine experiments.

The first distillation column used may in principle be any distillation column which satisfies the technical boundary conditions, in particular the separating performance desired, the temperature stability required, the pressure stability required and the material stability demanded. In general, these are columns having a metal jacket and both separating and nonseparating internals. Useful separating internals include, for example, trays or structured packings.

In the process according to the invention, it is generally advantageous to design and to operate the first distillation column in such a way that ≧50% by weight, preferably ≧75% by weight and more preferably ≧90% by weight of the amount of alcohol (II) fed in with the mixture is withdrawn via the bottom product.

The concentration of the alcohol (II) in the stream to be withdrawn as the bottom product is generally ≧90% by weight and preferably ≧95% by weight.

In the second distillation column, the azeotrope containing vinyl ether (I) and alcohol (II) from the first distillation column is separated into an azeotrope containing vinyl ether (I) and alcohol (II) as the top product and the vinyl ether (I) as the bottom product or as a gaseous sidestream in the stripping section.

In general, the second distillation column is operated at a temperature of from 75 to 225° C. and preferably from 100 to 175° C., measured in the bottom of the column, the temperature to be selected depending mainly upon the vinyl ether (I) and alcohol (II) to be separated and the pressure selected in the distillation column. In order to achieve an appropriate separation into an azeotrope containing vinyl ether (I) and alcohol (II), and a vinyl ether (I) stream, the second distillation column is operated at a pressure which is from 0.01 to 3 MPa higher compared to the first distillation column. Preference is given to operating the second distillation column at a pressure which is from 0.1 to 2 MPa higher compared to the first distillation column. A significant parameter in the determination of the pressure to be employed is the desired separating performance. In general, the higher the pressure differential to the first distillation column, the higher the separating performance in the second distillation column. The proportion of vinyl ether (I) also rises with increasing pressure differential to the first distillation column, and the vinyl ether may be withdrawn as a bottom product or as a gaseous sidestream in the stripping section. The remaining azeotrope thus has a lower vinyl ether (I) content at high pressure, which ultimately reduces the flow rate to and the loading of the first distillation column. On the other hand, it is to be noted that more compression energy is required with increasing pressure differential, the second distillation column should be designed appropriately for corresponding pressure, and that the distillation temperature also rises for a specific mixture to be separated, which leads to higher thermal stress on the products to be separated. The temperature to be selected and the pressure to be selected in each case for a specific system may be determined by those skilled in the art by simple calculation or simple routine experiments. For each specific system, there exists a relationship between temperature and pressure, so that the parameter range to be employed is generally dictated by technical (for example design of the distillation column separating performance mass flows), economic (for example capital costs and/or energy costs) and chemical (for example only insignificant, if any, decomposition of the products), boundary conditions.

In general, the number of theoretical plates in the second distillation column is from 5 to 75, the number of theoretical plates to be used for a specific system depending mainly upon the vinyl ether (I) and alcohol (II) to be separated, and also upon the separating performance expected. The number of theoretical plates to be selected in each case for a specific system may be determined by those skilled in the art by simple calculation or simple routine experiments.

The second distillation column used may in principle be any distillation column which satisfies the technical boundary conditions, in particular the separating performance desired, the temperature stability required, the pressure stability required and the material stability demanded. In general, these are columns having a metal jacket and both separating and nonseparating internals. Useful separating internals include, for example, trays or structured packings.

In the second distillation column, the vinyl ether (I) is withdrawn in liquid form as a bottom product or in gaseous form as a sidestream in the stripping section. In the latter case, the vinyl ether (I) is removed preferably in the region of the lower 25% and more preferably in the region of the lower 10%, of the total number of theoretical plates. For example, the formulation in the region of the lower 25% of the total number of the theoretical plates in a distillation column having a total 75 theoretical plates means that the gaseous sidestream is withdrawn in the region of the first to 19th theoretical plate. The advantage of the gaseous sidestream lies in the improvement of the color number of the vinyl ether (I) to be obtained in pure form, since undesired low boilers can be kept out of the product.

In the process according to the invention, it is generally advantageous to design and to operate the second distillation column in such a way that ≧20%, preferably ≧50%, more preferably ≧75% and most preferably ≧90% of the amount of vinyl ether (I) fed in with the mixture is withdrawn via the bottom product. Values of <20% generally lead to huge and thus uneconomic recycle streams. The concentration of the vinyl ether (I) in the stream to be withdrawn as a bottom product is generally ≧97.5% by weight and preferably ≧99.5% by weight.

FIG. 1 shows a simplified block diagram of the process according to the invention. The stream (a) containing vinyl ether (I) and alcohol (II) to be separated is fed to the first distillation column A via line (1). The bottom product withdrawn is a stream (b) enriched with alcohol (II) via line (2). The azeotrope containing vinyl ether (I) and alcohol (II) which is withdrawn as a top product is fed via line (3) to the second distillation column B. The vinyl ether (I) (c) is withdrawn from here via line (4a) as a bottom product or via line (4b) as a gaseous sidestream in the stripping section. The azeotrope containing vinyl ether (I) and alcohol (II) which is withdrawn as a top product is recycled via line (5) to the first distillation column A.

Since the vinyl ether (I) withdrawn as a bottom product or as a gaseous sidestream in the stripping section of the second distillation column is generally still contaminated with minor secondary components, for example acetals, preference is given to passing it into a purifying distillation column and obtaining the purified vinyl ether (I) as a top product. The design of the purifying distillation column and the distillation parameters may be determined by those skilled in the art by simple calculation or simple routine experiments.

Figure 2:
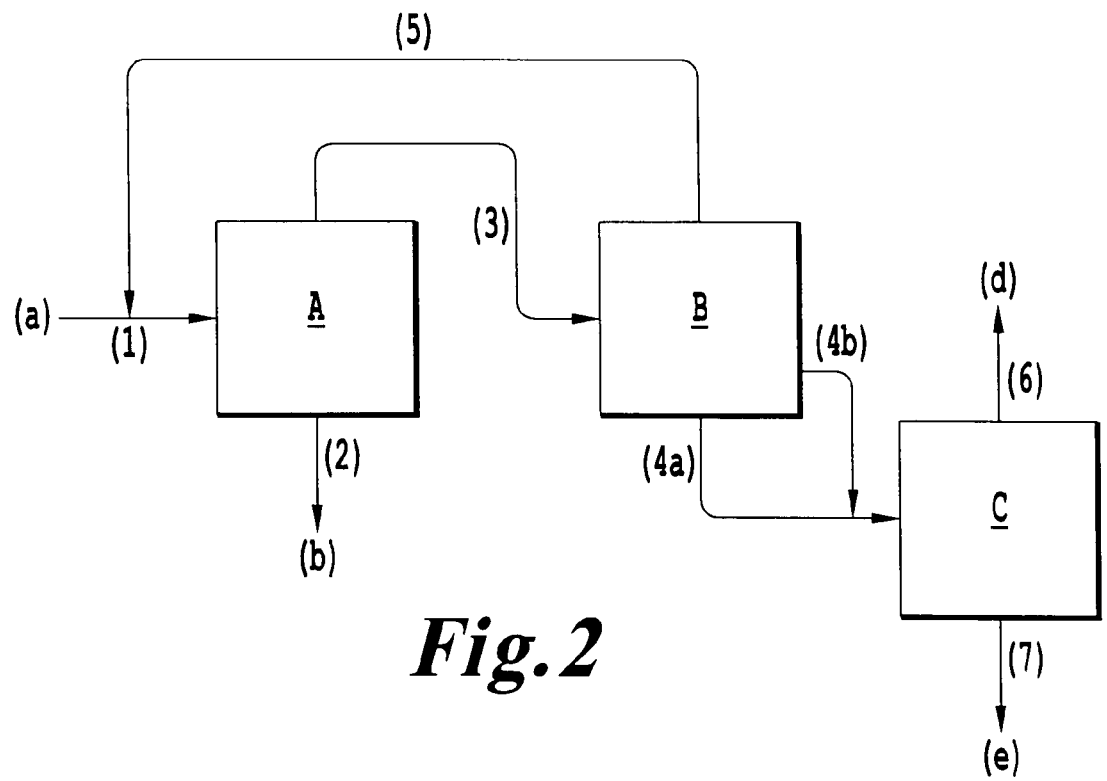
FIG. 2 shows a block diagram of a preferred process of the invention.

FIG. 2 shows a simplified block diagram of this preferred process according to the invention. The stream containing vinyl ether (I) withdrawn as a bottom product or as a gaseous sidestream in the stripping section of the second distillation column is fed via line (4a) or (4b) to the purifying distillation column C. The bottom product withdrawn via line (7) is a stream comprising the higher-boiling secondary components (e). The purified vinyl ether (I) (d) is withdrawn as a top product via line (6).

The mixture to be used in the process according to the invention contains a vinyl ether of the general formula (I)

$$R^1-O-CH=CH_2 \qquad (I)$$

and an alcohol of the general formula (II)

$$R^2-OH \qquad (II)$$

in which the $R^1$ and $R^2$ radicals are each independently a saturated or unsaturated, aliphatic or cycloaliphatic radical having from 2 to 10 carbon atoms, and in which the alcohol (II) has a boiling point which is at least 1° C. higher, measured at or extrapolated to 0.1 MPa abs, than the vinyl ether (I).

The alcohol (II) preferably has a boiling point which is at least 2° C. and more preferably at least 5° C., higher, measured at or extrapolated to 0.1 MPa abs, than the vinyl ether (I).

Preferred saturated or unsaturated, aliphatic or cycloaliphatic $R^1$ and $R^2$ radicals having from 2 to 10 carbon atoms include $C_2$- to $C_{10}$-alkyl radicals, for example ethyl, 1-propyl, 2-propyl (isopropyl), 1-butyl, 2-butyl (sec-butyl), 2-methyl-1-propyl (isobutyl), 2-methyl-2-propyl (tert-butyl), 1-pentyl, 2-pentyl, 3-pentyl, 3-methyl-2-butyl, 2-methyl-2-butyl, 1-hexyl, 1-heptyl, 1-octyl, 2-ethyl-1-hexyl, 1-nonyl, 1-decyl;

$C_2$- to $C_{10}$-alkenyl radicals, for example ethenyl (vinyl), 1-prop-1-enyl, 2-prop-1-enyl, 3-prop-1-enyl, 1-but-1-enyl, 2-but-1-enyl, 3-but-1-enyl, 4-but-1-enyl, 1-but-2-enyl, 2-but-2-enyl, 3-but-2-enyl, 4-but-2-enyl;

$C_2$- to $C_{10}$-cycloalkyl radicals, for example cyclopentyl, 2-methylcyclopentyl, 3-methylcyclopentyl, cyclohexyl, 2-methylcyclohexyl, 3-methylcyclohexyl, 4-methylcyclohexyl, cycloheptyl, cyclooctyl;

$C_2$- to $C_{10}$-cycloalkenyl radicals, for example 1-cyclopent-1-enyl, 3-cyclopent-1-enyl, 4-cyclopent-1-enyl, 1-cyclohex-1-enyl, 3-cyclohex-1-enyl, 4-cyclohex-1-enyl.

In the process according to the invention, particular preference is given to using a mixture containing a vinyl ether (I) and alcohol (II) in which the $R^1$ and $R^2$ radicals are each independently a $C_2$- to $C_4$-alkyl radical, in particular ethyl, 1-propyl, 2-propyl (isopropyl), 1-butyl, 2-butyl (sec-butyl), 2-methyl-1-propyl (isobutyl) and 2-methyl-2-propyl (tert-butyl).

In the process according to the invention, very particular preference is given to using a mixture containing vinyl ether (I) and alcohol (II) in which the $R^1$ and $R^2$ radicals are identical. Very particular preference is therefore given to using the following mixtures containing vinyl ether (I) and alcohol (II):
  ethyl vinyl ether and ethanol,
  1-propyl vinyl ether and 1-propanol;
  2-propyl vinyl ether and 2-propanol;
  1-butyl vinyl ether and 1-butanol;
  2-butyl vinyl ether and 2-butanol;
  isobutyl vinyl ether and isobutanol;
  tert-butyl vinyl ether and tert-butanol.

In a preferred embodiment of the process according to the invention, the mixture used which contains vinyl ether (I) and alcohol (II) stems from the vinyl ether synthesis by reacting the alcohol (II) with ethyne in the presence of a basic alkali metal or alkaline earth metal compound, distillatively removing low boilers and high boilers from the bottom product enriched with the alcohol (II) in the first distillation column and recycling the purified alcohol (II) back to the vinyl ether synthesis. The synthetic processes for preparing vinyl ethers by reacting the alcohol (II) with ethyne in the presence of a basic alkali metal or alkaline earth metal compound are generally known and are described, for example, in Ullmann's Encyclopedia of Industrial Chemistry, 6$^{th}$ edition, 2000 Electronic Release, Chapter "VINYLETHERS—Production" or W. Reppe et al., Justus Liebigs Ann. Chem., 601 (1956), pages 135 to 138 and the documents cited therein.

In the aforementioned preferred process according to the invention, the low boilers and high boilers are removed by distillation from the bottom product enriched with the alcohol (II) from the first distillation column in a dividing wall column or an arrangement of distillation columns which are conventional or have heat and/or mass transfer. Particular preference is given to effecting the distillative separation mentioned in a dividing wall column or an arrangement of distillation columns having heat and/or mass transfer.

Figure 3:
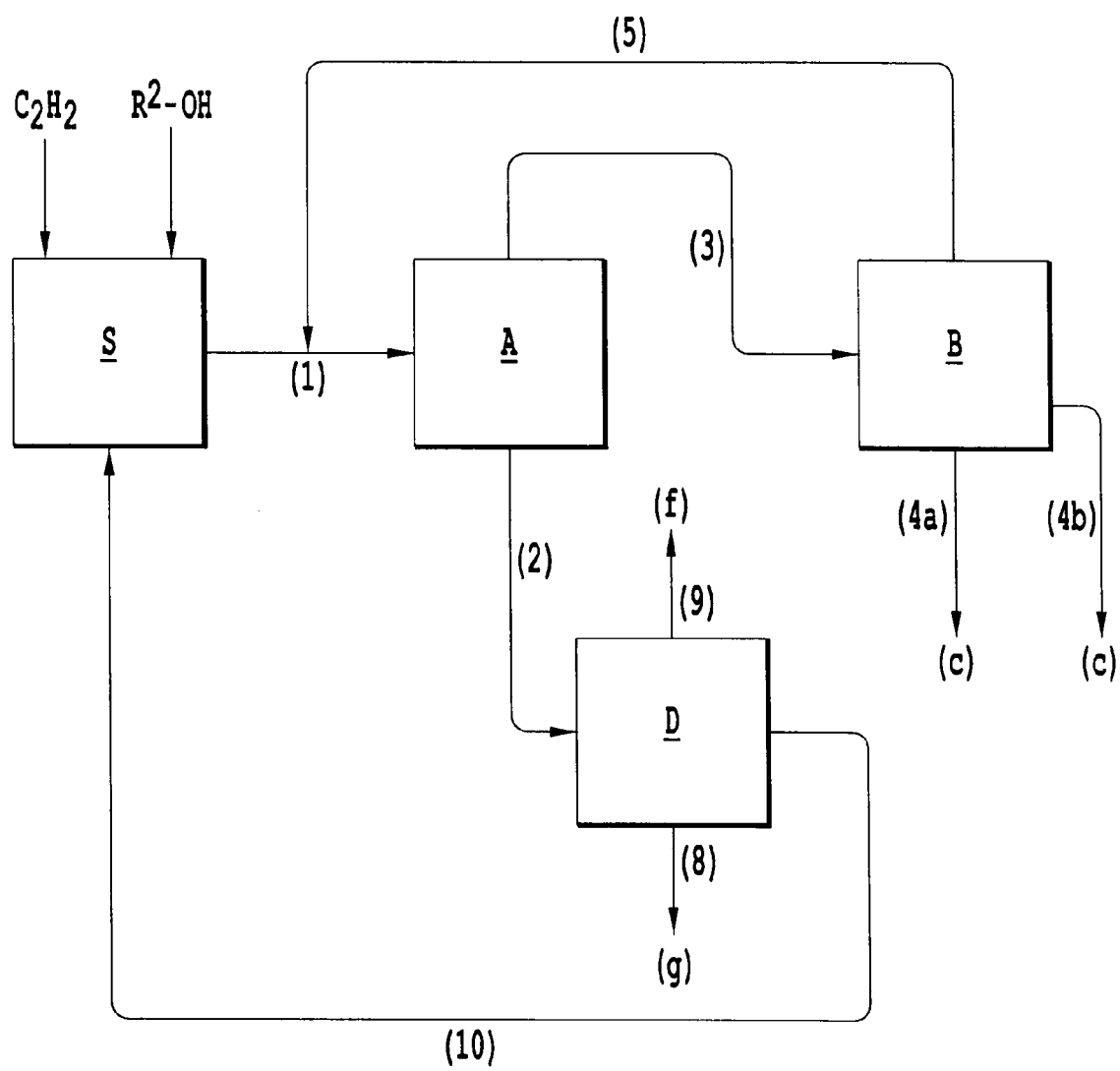
FIG. 3 shows a preferred embodiment of the invention.

FIG. 3 shows a simplified block diagram of this preferred process according to the invention. The stream containing alcohol (II) withdrawn as the bottom product of the first distillation column is conducted via line (2) to the dividing wall column D or to an arrangement of distillation columns which are conventional or have thermal and/or mass transfer.

It is separated there into low boilers (f) which are withdrawn via line (9) as a top product and into high boilers (g) which are withdrawn via line (8) as a bottom product. The purified alcohol (II) is withdrawn as a sidestream from the dividing wall column D or from the arrangement of distillation columns which are conventional or have heat and/or mass transfer, and recycled via line (10) to the synthesis stage S.

In a preferred embodiment of the process according to the invention, a mixture is used which contains vinyl ether (I) and alcohol (II) and stems from the vinyl ether synthesis by reacting the alcohol (II) with ethyne in the presence of a basic alkali metal or alkaline earth metal compound, and in which the $R^1$ and $R^2$ radicals are identical and are each a $C_2$- to $C_4$-alkyl radical. This mixture is separated in a similar manner to the description for the simplified block diagram of FIG. 1 into a stream containing alcohol (II) and a stream containing vinyl ether (I). If, as a consequence of the achieved and desired purity of the stream containing the alcohol (II), further purification is necessary, preference is given to purifying in a similar manner to the description for the simplified block diagram of FIG. 3 by a subsequent distillation in a dividing wall column or an arrangement of distillation columns having thermal and/or mass transfer. The resulting stream containing alcohol (II) is subsequently recycled to the synthesis stage. The stream containing vinyl ether (I) is purified in a similar manner to the description for the simplified block diagram of FIG. 2 by a subsequent distillation, and the purified vinyl ether (I) is obtained as a top product.

In the preferred embodiment mentioned, the first distillation column generally has from 5 to 75 theoretical plates and is operated at a pressure of from 0.01 to 1 MPa abs, measured at the top of the column, and a temperature of from 75 to 225° C., measured in the bottom of the column. The second distillation column generally has from 5 to 75 theoretical plates and is operated at a pressure which is from 0.1 to 2 MPa higher than the first distillation column and a temperature of from 75 to 225° C., measured in the bottom of the column. If the vinyl ether (I) is withdrawn from the second distillation column as a gaseous sidestream in the stripping section, this sidestream is generally in the region of the first to the tenth and preferably in the region of the first to the second, theoretical plate.

The process according to the invention enables the separation of a mixture containing vinyl ether and alcohol, which leads to purified vinyl ether and alcohol, in particular at low cost and inconvenience with regard to apparatus and process, with high plant capacity and without the risk of contamination of the vinyl ether and/or the alcohol by the addition of extraneous substances as auxiliaries.

We claim:

1. A process for distillatively separating a mixture comprising a vinyl ether of the general formula (I)

and alcohol of the general formula (II)

wherein $R^1$ and $R^2$ are each independently a $C_2$-$C_4$-alkyl radical, and the alcohol (II) has a boiling point which is at least 1° C. higher, measured at or extrapolated to 0.1 MPa abs, than the vinyl ether (I), comprising:

a) passing the mixture into a first distillation column and withdrawing, as a top product, an azeotrope comprising vinyl ether (I) and alcohol (II) and, as a bottom product, a stream enriched with the alcohol (II);

b) passing the azeotrope comprising vinyl ether (I) and alcohol (II) from the first distillation column into a second distillation column which is operated at a pressure which is from 0.01 to 3 MPa higher compared to the first distillation column, and withdrawing the vinyl ether, as a gaseous sidestream in a stripping section of the second distillation column in a region of the lower 25% of a total number of theoretical plates, and, as a top product, an azeotrope comprising vinyl ether (I) and alcohol (II); and c) recycling the azeotrope comprising vinyl ether (I) and alcohol (II) from the second distillation column into the first distillation column.

2. The process according to claim 1, wherein the $R^1$ and $R^2$ radicals are identical.

3. The process according to claim 2, wherein the vinyl ether and the alcohol respectively are selected from the group consisting of ethyl vinyl ether and ethanol, 1-propyl vinyl ether and 1-propanol, 2-propyl vinyl ether and 2-propanol, 1-butyl vinyl ether and 1-butanol, 2-butyl vinyl ether and 2-butanol, isobutyl vinyl ether and isobutanol and tert-butyl vinyl ether and tert-butanol.

4. The process according to claim 1, further comprising:
distillatively removing low boilers and high boilers from the bottom product enriched with the alcohol (II) in the first distillation column to form a purified alcohol II and
recycling the purified alcohol (II) to a vinyl ether (I) synthesis wherein the vinyl ether (I) synthesis comprises:
reacting the alcohol (II) with an ethyne in the presence of a basic alkali metal or alkaline earth metal compound.

5. The process according to claim 4, wherein the distillative removal of low boilers and high boilers from the bottom product enriched with the alcohol (II) in the first distillation column is carried out in a dividing wall column or an arrangement of distillation columns having heat and/or mass transfer.

6. The process according to claim 4, wherein the $R^1$ and $R^2$ radicals are identical.

7. The process according to claim 6, wherein the vinyl ether and the alcohol respectively are selected from the group consisting of ethyl vinyl ether and ethanol, 1-propyl vinyl ether and 1-propanol, 2-propyl vinyl ether and 2-propanol, 1-butyl vinyl ether and 1-butanol, 2-butyl vinyl ether and 2-butanol, isobutyl vinyl ether and isobutanol and tert-butyl vinyl ether and tert-butanol.

8. The process according to claim 1, further comprising:
passing the vinyl ether (I) withdrawn from the second distillation column as gaseous sidestream in the stripping section into a purifying distillation column and
obtaining purified vinyl ether (I) from the purifying distillation column as a top product.

9. The process according to claim 8, further comprising:
distillatively removing low boilers and high boilers from the bottom product enriched with the alcohol (II) in the first distillation column and
recycling the purified alcohol (II) to a vinyl ether (I) synthesis wherein the vinyl ether (I) synthesis comprises:
reacting the alcohol (II) with an ethyne in the presence of a basic alkali metal or alkaline earth metal compound.

10. The process according to claim 9, wherein the distillative removal of low boilers and high boilers from the bottom product enriched with the alcohol (II) in the first distillation column is carried out in a dividing wall column or an arrangement of distillation columns having heat and/or mass transfer.

* * * * *

UNITED STATES PATENT AND TRADEMARK OFFICE
CERTIFICATE OF CORRECTION

PATENT NO.        : 7,670,464 B2                                                Page 1 of 1
APPLICATION NO.   : 10/560135
DATED             : March 2, 2010
INVENTOR(S)       : Klass et al.

It is certified that error appears in the above-identified patent and that said Letters Patent is hereby corrected as shown below:

On the title page, Item (54), and Column 1, the title information is incorrect. Item (54) and Column 1 should read:

-- (54)  METHOD FOR THE DISTILLATIVE
         SEPARATION OF A MIXTURE CONTAINING
         VINYL ETHER AND ALCOHOL --

Signed and Sealed this

Twenty-third Day of November, 2010

David J. Kappos
*Director of the United States Patent and Trademark Office*